United States Patent
Satoh

(10) Patent No.: US 10,024,825 B2
(45) Date of Patent: Jul. 17, 2018

(54) WAFER CLAMP DETECTION BASED ON VIBRATION OR ACOUSTIC CHARACTERISTIC ANALYSIS

(71) Applicant: Axcelis Technologies, Inc., Beverly, MA (US)

(72) Inventor: Shu Satoh, Byfield, MA (US)

(73) Assignee: Axcelis Technologies, Inc., Beverly, MA (US)

(*) Notice: Subject to any disclaimer, the term of this patent is extended or adjusted under 35 U.S.C. 154(b) by 238 days.

(21) Appl. No.: 14/963,703

(22) Filed: Dec. 9, 2015

(65) Prior Publication Data

US 2016/0187302 A1 Jun. 30, 2016

Related U.S. Application Data

(60) Provisional application No. 62/096,924, filed on Dec. 26, 2014.

(51) Int. Cl.
| | | |
|---|---|---|
| *G01H 13/00* | (2006.01) | |
| *G01N 29/34* | (2006.01) | |
| *H01L 21/67* | (2006.01) | |
| *G01N 29/09* | (2006.01) | |
| *G01N 29/12* | (2006.01) | |

(Continued)

(52) U.S. Cl.
CPC .............. *G01N 29/34* (2013.01); *G01H 13/00* (2013.01); *G01N 29/09* (2013.01); *G01N 29/12* (2013.01); *G01N 29/2418* (2013.01); *H01L 21/67259* (2013.01); *H01L 21/67288* (2013.01); *H01L 21/6831* (2013.01); *H01L 22/10* (2013.01); *G01N 2291/014* (2013.01); *G01N 2291/018* (2013.01); *G01N 2291/028* (2013.01)

(58) Field of Classification Search
CPC .............. G01H 13/00; G01N 2291/014; H01L 21/6831
USPC .......................................................... 73/579
See application file for complete search history.

(56) References Cited

U.S. PATENT DOCUMENTS

| | | | | |
|---|---|---|---|---|
| 6,041,642 | A * | 3/2000 | Duncan .................... | G01G 3/16 422/88 |
| 7,073,383 | B2 * | 7/2006 | Jones ...................... | G01N 29/11 73/627 |
| 7,854,167 | B2 * | 12/2010 | Hashiba ............... | G01N 29/045 73/572 |

* cited by examiner

*Primary Examiner* — John Chapman, Jr.
(74) *Attorney, Agent, or Firm* — Eschweiler & Potashnik, LLC

(57) ABSTRACT

A workpiece clamping status detection system and method for detecting a clamping state of a clamping device is provided. A clamping device having a clamping surface is configured to selectively clamp a workpiece to the clamping surface. The clamping device may be an electrostatic chuck or a mechanical clamp for selectively securing a semiconductor wafer thereto. A vibration-inducing mechanism is further provided, wherein the vibration-inducing mechanism is configured to selectively vibrate one or more of the clamping device and workpiece. A vibration-sensing mechanism is also provided, wherein the vibration-sensing mechanism is configured to detect the vibration of the one or more of the clamping device and workpiece. Detection of clamping status utilizes changes in acoustic properties, such as a shift of natural resonance frequency or acoustic impedance, to determine clamping condition of the workpiece. A controller is further configured to determine a clamping state associated with the clamping of the workpiece to the clamping surface, wherein the clamping state is associated with the detected vibration of the one or more of the clamping device and workpiece.

16 Claims, 3 Drawing Sheets

(51) Int. Cl.
*G01N 29/24* (2006.01)
*H01L 21/683* (2006.01)
*H01L 21/66* (2006.01)

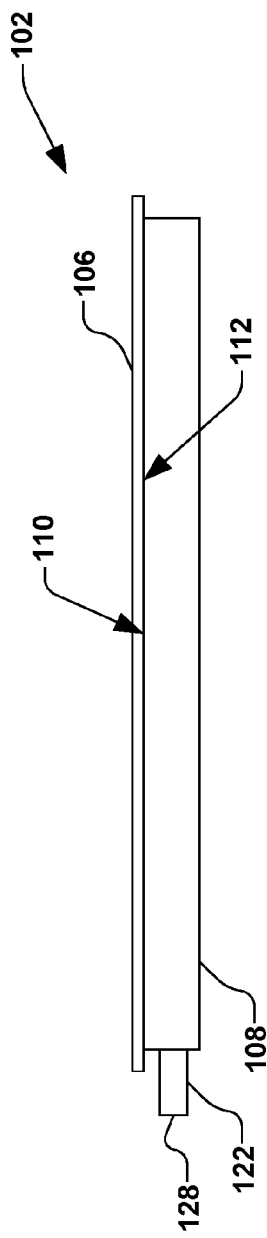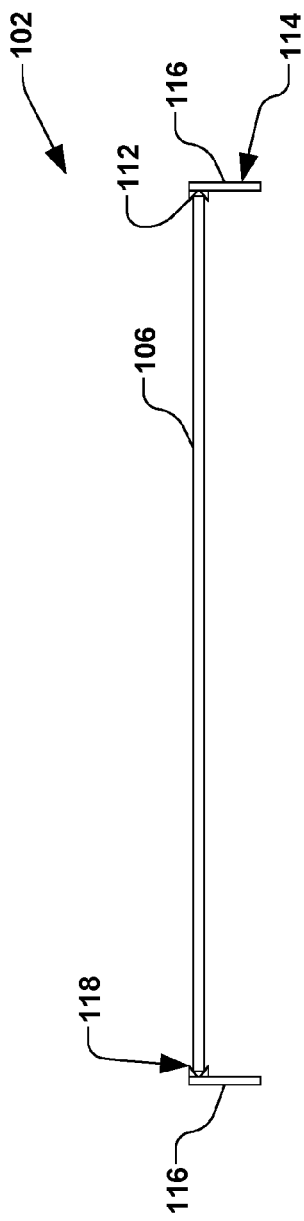

WAFER CLAMP DETECTION BASED ON VIBRATION OR ACOUSTIC CHARACTERISTIC ANALYSIS

REFERENCE TO RELATED APPLICATION

This application claims priority to and the benefit of U.S. Provisional Application Ser. No. 62/096,924 which was filed Dec. 26, 2014, entitled "WAFER CLAMP DETECTION BASED ON VIBRATION OR ACOUSTIC CHARACTERISTIC ANALYSIS", the entirety of which is hereby incorporated by reference as if fully set forth herein.

TECHNICAL FIELD

The present invention relates generally to workpiece clamping systems, and more specifically to detection of a workpiece in a clamp comprising an electrostatic clamp.

BACKGROUND

Electrostatic clamps or chucks (ESCs) are often utilized in the semiconductor industry for clamping workpieces or substrates during plasma-based or vacuum-based semiconductor processes such as ion implantation, etching, chemical vapor deposition (CVD), etc. Clamping capabilities of the ESCs, as well as workpiece temperature control, have proven to be quite valuable in processing semiconductor substrates or wafers, such as silicon wafers. A typical ESC, for example, comprises a dielectric layer positioned over a conductive electrode, wherein the semiconductor wafer is placed on a surface of the ESC (e.g., the wafer is placed on a surface of the dielectric layer). During semiconductor processing (e.g., ion implantation), a clamping voltage is typically applied between the wafer and the electrode, wherein the wafer is clamped against the chuck surface by electrostatic forces.

During workpiece handling and/or processing of workpieces, it is often necessary to verify and/or ensure adequate clamping of the workpiece to the ESC. Furthermore, For certain processes, such as certain ion implantation processes, cooling the workpiece via a cooling of the ESC is desirable, wherein a clamping force between the workpiece and the ESC ensures adequate cooling of the workpiece. Consequently, various configurations for verifying workpiece clamping status have been instituted. One common workpiece verification is based on a change in capacitance associated with the workpiece and ESC, wherein a proximity of the workpiece to the ESC surface generally defines a capacitance between the workpiece and ESC surface. However, such a measured capacitance does not always indicate whether the workpiece is adequately gripped or clamped to the ESC.

Therefore, a need exists in the art for an apparatus, system, and method for determining whether a workpiece is adequately gripped or clamped to a surface of an ESC.

SUMMARY

The present invention overcomes the limitations of the prior art by providing a system, apparatus, and method for determining a clamping status of a workpiece with respect to an electrostatic clamp. Accordingly, the following presents a simplified summary of the disclosure in order to provide a basic understanding of some aspects of the invention. This summary is not an extensive overview of the invention. It is intended to neither identify key or critical elements of the invention nor delineate the scope of the invention. Its purpose is to present some concepts of the invention in a simplified form as a prelude to the more detailed description that is presented later.

In accordance with the present disclosure, a workpiece clamping status detection system is provided, wherein a clamping device has a clamping surface associated therewith, and wherein the clamping device is configured to selectively clamp a workpiece to the clamping surface. The clamping device, for example, comprises an electrostatic clamp, and wherein the clamping surface comprises a generally planar surface configured to electrostatically clamp the workpiece thereto. Alternatively, the clamping device comprises a mechanical clamp, wherein the mechanical clamp comprises one or more grippers configured to selectively grip a peripheral edge of the workpiece. In another alternative, the clamping device comprises any clamping apparatus configured to selectively retain the workpiece thereto.

According to one example, a vibration-inducing mechanism is provided, wherein the vibration-inducing mechanism is configured to selectively vibrate one or more of the clamping device and workpiece. Further, a vibration-sensing mechanism is provided, wherein the vibration-sensing mechanism is configured to detect the vibration of the one or more of the clamping device and workpiece. In one example, the vibration-inducing mechanism, for example, comprises an electromechanical vibration transmitter. In such an example, the vibration-sensing mechanism may comprise an accelerometer. In an example where the detection is to be performed in atmosphere, the vibration-inducing mechanism may comprise an audio speaker and is the vibration-sensing mechanism may comprise a microphone. Alternatively, the vibration-inducing mechanism comprises an ultrasound emitter, and wherein the vibration-sensing mechanism comprises an ultrasound receiver. On some electromechanical vibration transmitters, such as a voice coil of an audio speaker or ultrasound transmitter, the transmitter may be also configured to operate as a sensing mechanism.

In another example, the vibration-sensing mechanism comprises a laser apparatus. The laser apparatus, for example, is configured to direct a laser beam toward a surface of the workpiece, wherein the laser apparatus is further configured to detect a modulation of a received reflection of the laser beam from the surface of the workpiece. The modulation of the received reflection of the laser beam is thus associated with the vibration of the workpiece with respect to the clamping device.

In accordance with yet another example, a controller is provided and configured to determine a clamping state associated with the clamping of the workpiece to the clamping surface. The clamping state, for example, is associated with the detected vibration of the one or more of the clamping device and workpiece. In one example, the controller is configured to differentiate an impedance pattern associated with the clamping state.

According to yet another exemplary aspect, a method for detecting a clamping status of a workpiece in a clamping device is provided within the present disclosure. The method, in one example, comprises clamping a surface of the workpiece to a clamping surface of the clamping device, and inducing a vibration within one or more of the clamping device and workpiece. The vibration of the one or more of the clamping device and workpiece is subsequently detected, and a clamping state associated with the clamping of the workpiece to the clamping surface is thereby determined. The clamping state, for example, is associated with a shift of resonant frequency of the detected vibration of the one or more of the clamping device and workpiece.

The above summary is merely intended to give a brief overview of some features of some embodiments of the present invention, and other embodiments may comprise additional and/or different features than the ones mentioned above. In particular, this summary is not to be construed to be limiting the scope of the present application. Thus, to the accomplishment of the foregoing and related ends, the invention comprises the features hereinafter described and particularly pointed out in the claims. The following description and the annexed drawings set forth in detail certain illustrative embodiments of the invention. These embodiments are indicative, however, of a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 2 is a cross-sectional view of an exemplary electrostatic clamp in accordance with another aspect of the disclosure.

FIG. 3 is a cross-sectional view of an exemplary mechanical clamp in accordance with yet another aspect of the disclosure.

DETAILED DESCRIPTION

Figure 1:
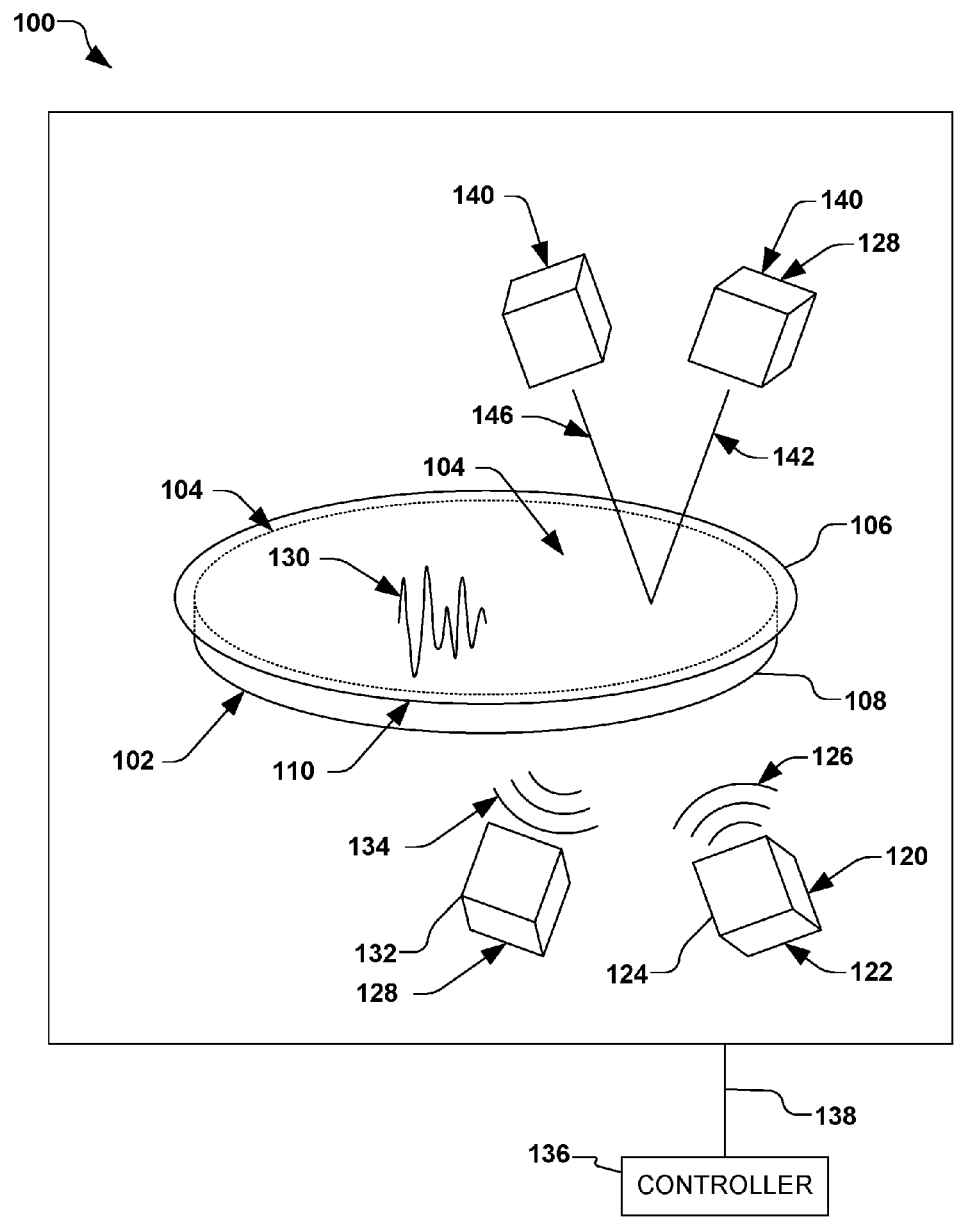
FIG. 1 is a block diagram of an exemplary workpiece clamping status detection system in accordance with several aspects of the present disclosure.

The present disclosure is directed generally toward a system, apparatus, and method for detecting a clamping status of a workpiece to a workpiece clamp. Accordingly, the present invention will now be described with reference to the drawings, wherein like reference numerals may be used to refer to like elements throughout. It is to be understood that the description of these aspects are merely illustrative and that they should not be interpreted in a limiting sense. In the following description, for purposes of explanation, numerous specific details are set forth in order to provide a thorough understanding of the present invention. It will be evident to one skilled in the art, however, that the present invention may be practiced without these specific details. Further, the scope of the invention is not intended to be limited by the embodiments or examples described hereinafter with reference to the accompanying drawings, but is intended to be only limited by the appended claims and equivalents thereof.

It is also noted that the drawings are provided to give an illustration of some aspects of embodiments of the present disclosure and therefore are to be regarded as schematic only. In particular, the elements shown in the drawings are not necessarily to scale with each other, and the placement of various elements in the drawings is chosen to provide a clear understanding of the respective embodiment and is not to be construed as necessarily being a representation of the actual relative locations of the various components in implementations according to an embodiment of the invention. Furthermore, the features of the various embodiments and examples described herein may be combined with each other unless specifically noted otherwise.

It is also to be understood that in the following description, any direct connection or coupling between functional blocks, devices, components, circuit elements or other physical or functional units shown in the drawings or described herein could also be implemented by an indirect connection or coupling. Furthermore, it is to be appreciated that functional blocks or units shown in the drawings may be implemented as separate features or circuits in one embodiment, and may also or alternatively be fully or partially implemented in a common feature or circuit in another embodiment. For example, several functional blocks may be implemented as software running on a common processor, such as a signal processor. It is further to be understood that any connection which is described as being wire-based in the following specification may also be implemented as a wireless communication, unless noted to the contrary.

In accordance with one aspect of the present disclosure, FIG. 1 illustrates an exemplary workpiece clamping status detection system 100. The workpiece clamping status detection system 100, for example, comprises a clamping device 102 having a clamping surface 104 associated therewith, wherein the clamping device is configured to selectively clamp a workpiece 106 to the clamping surface. The clamping device 102, for example, comprises an electrostatic clamp 108 (also called an "ESC") configured to electrostatically clamp the workpiece 106 (e.g., a semiconductor such as a silicon wafer, a display panel, etc.). The clamping surface 104, for example, comprises a generally planar surface 110, as illustrated in FIG. 2. The generally planar surface 110, for example, is configured to selectively clamp a surface 112 of the workpiece 106 thereto via electrostatic attraction, as will be understood by one of ordinary skill in the art.

In one alternative, the clamping device 102 of FIG. 1 comprises a mechanical clamp 114, an example of which is illustrated in FIG. 3. The mechanical clamp 114 illustrated in FIG. 3, for example, comprises one or more grippers 116 configured to selectively grip a peripheral edge 118 of the workpiece 106. Alternatively, the mechanical clamp 114 may comprise any mechanical device configured to selectively retain the workpiece 106.

In accordance with the present disclosure, as illustrated in FIG. 1, a vibration-inducing mechanism 120 is provided, wherein the vibration-inducing mechanism is configured to selectively vibrate one or more of the clamping device 102 and workpiece 106. The vibration-inducing mechanism 120, for example, comprises an acoustic device 122 such as a speaker 124 configured to produce sound waves 126 if the detection is to be made in atmosphere. It should be understood that the acoustic device 122 may comprise any wave-emitting device or device capable of inducing vibration.

Furthermore, a vibration-sensing mechanism 128 is provided, wherein the vibration-sensing mechanism is configured to detect a vibration 130 of the one or more of the clamping device 102 and workpiece 106. For example, the vibration-sensing mechanism 128 comprises a microphone 132 configured to detect reflected sound waves 134 from the acoustic device 122 if the detection is made in atmosphere. In another example, the vibration-inducing mechanism 120 comprises an ultrasound emitter, and wherein the vibration-sensing mechanism 128 comprises an ultrasound receiver. In yet another example, when detection in a vacuum is desired, or in instances using ultrasound, the vibration-inducing mechanism 120 and vibration-sensing mechanism 128 (e.g., an ultrasound transducer which combines transmitter and receiver) may be physically attached to the clamping device 102 as illustrated in FIG. 2 (e.g., coupled to the surface 110) for conduction of acoustic wave through the substantially solid mediums of the clamping device. Alternatively, the vibration-inducing mechanism 120 and vibration-sensing mechanism 128 of FIG. 1 may be coupled to the clamping device 102 via any generally rigid structure coupled to the clamping device, such as scan arm (not shown) configured to translate the clamping device.

A controller 136, for example, is further provided and configured to determine a clamping state 138 associated with the clamping of the workpiece 106 to the clamping surface 104 of the clamping device 102. The clamping state 138, for example, is associated with the detected vibration 130 of the one or more of the clamping device 102 and workpiece 106. According to one example, the controller 136 is configured to differentiate an impedance pattern associated with the clamping state 138.

In accordance with another example, aspect, the vibration-sensing mechanism 128 comprises a laser apparatus 140. The laser apparatus 140, for example, is configured to direct a laser beam 142 toward a surface 144 of the workpiece 106 and to detect a modulation of a received reflection 146 of the laser beam 142 from the surface of the workpiece. Accordingly, the modulation of the received reflection 146 of the laser beam 142 is associated with the vibration 130 of the workpiece 106 with respect to the clamping device 102. According to another example, another laser apparatus (not shown) is configured to direct another laser beam (not shown) toward the clamping device 102, whereby the controller 136, for example, is further configured to compare the modulations of the received deflections associated with the respective workpiece 106 and the clamping device, thus further determining the clamping state of the workpiece to the surface 104 of the clamping device. For example, if the workpiece 106 is not adequately clamped to the surface 104 of the clamping device 102, the modulations of the received deflections associated with the respective workpiece and the clamping device would differ, whereby the controller 136 is configured to determine the clamping state based on the difference of modulations.

Figure 4:
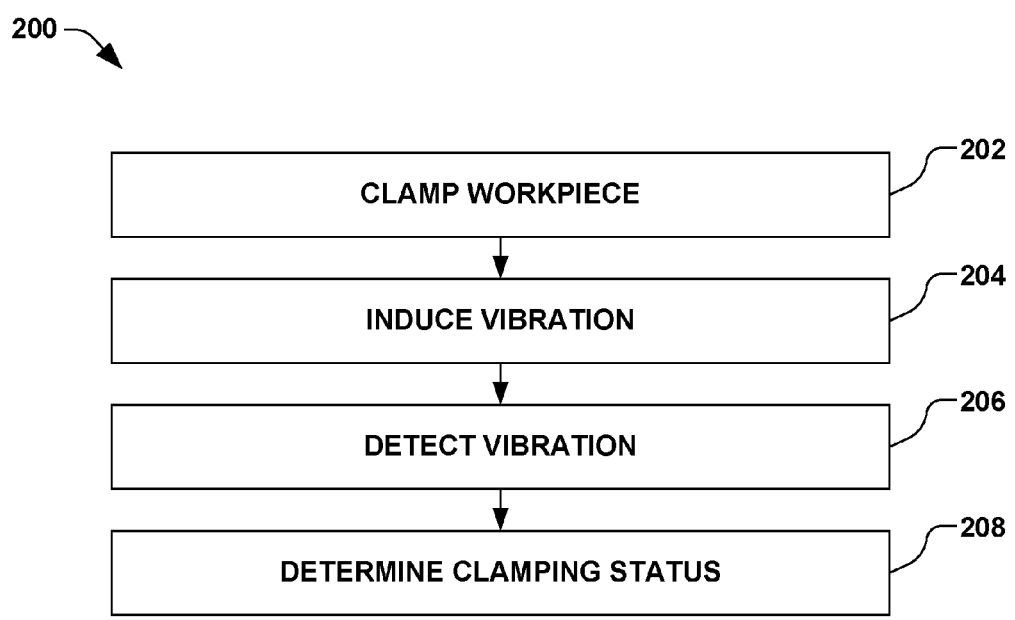
FIG. 4 illustrates a methodology for determining a clamping status of a workpiece in a clamp, in accordance with to still another aspect.

In accordance with another exemplary aspect of the invention, FIG. 4 illustrates an exemplary method 100 is provided for detecting a clamping status of an electrostatic clamp. It should be noted that while exemplary methods are illustrated and described herein as a series of acts or events, it will be appreciated that the present invention is not limited by the illustrated ordering of such acts or events, as some steps may occur in different orders and/or concurrently with other steps apart from that shown and described herein, in accordance with the invention. In addition, not all illustrated steps may be required to implement a methodology in accordance with the present invention. Moreover, it will be appreciated that the methods may be implemented in association with the systems illustrated and described herein as well as in association with other systems not illustrated.

The method 200 of FIG. 4 begins at act 202, wherein a surface of a workpiece is clamped to a clamping surface of a clamping device, such as the clamping device 102 of FIG. 1. A vibration is induced within one or more of the clamping device and workpiece in act 204, such as by emitting sound waves toward one or more of the clamping device and workpiece. In act 206, the vibration of the one or more of the clamping device and workpiece is detected. For example, detecting the vibration of the one or more of the clamping device and workpiece in act 206 comprises detecting the sound waves discussed above once the sound waves bounce off the one or more of the clamping device and workpiece. Alternatively, detecting the vibration of the one or more of the clamping device and workpiece in act 206 comprises directing a laser beam toward a surface of the workpiece and receiving a reflection of the laser beam from the surface of the workpiece, wherein a modulation of the received reflection of the laser beam from the surface of the workpiece is determined, and wherein the modulation of the received reflection of the laser beam is associated with the vibration of the workpiece with respect to the clamping device.

In act 208, a clamping state associated with the clamping of the workpiece to the clamping surface is determined, wherein the clamping state is associated with a shift of resonant frequency and Q of the resonance of the detected vibration of the one or more of the clamping device and workpiece. For example, the detected vibration in act 206 can be utilized to determine the level of clamping (e.g., the clamping state) in act 208 based on predetermined clamping profiles associated with the clamping device and workpiece in various stages of clamping and a comparison or other calculation associated therewith.

By introducing vibrational (e.g., acoustic) analysis in the sensing of workpieces, one can sense if a workpiece or wafer is dynamically tied (e.g., connected) to the ESC. The present disclosure thus advantageously provides a system and method to detect workpiece clamp status by changes in vibrational (or acoustical) characteristics when in a state where the workpiece is tightly clamped to ESC and in a state when the workpiece is simply sitting or resting on the ESC.

One example is to observe changes in natural resonance frequency of the ESC. For example, the present disclosure contemplates changes in natural resonance frequency between a state without a wafer on the ESC, another with a wafer on the ESC but not clamped, and yet another state with the wafer clamped to the ESC where the ESC and wafer vibrate together. Once a wafer is clamped to the ESC, for example, it will generally vibrate together with the ESC as one solid piece, and the present disclosure expects that its natural resonance frequency will be slightly lower than the case without a wafer at all. When a wafer is just sitting or resting on an ESC but not clamped thereto, the wafer is expected to be seen as a loosely coupled object to the ESC and the natural resonance frequency will be different from the two former cases.

To monitor natural resonance frequency, one method is to apply external vibration, such as a vibration of selectively variable frequency, and to monitor the displacement as the drive frequency is swept. In other examples, an impulse or a shock pulse can be applied as an exciter and the frequency component of the displacement signal can be monitored. Alternatively, machine noise can be used to excite its natural frequency.

Another example is to monitor two vibration frequencies, one from the ESC and the other from a wafer and compare the coherency between the two vibrations. The present disclosure expects that once a wafer is clamped to the ESC, the two vibrations would be generally coherent to indicate the clamp status. In one example, two vibrations are expected to be generally coherent at low frequency, even if a wafer is not clamped (e.g., simply riding or resting on the ESC). However, at a relatively high frequency (e.g., greater than 100 Hz), it is more likely that the coherency is a good indication of the wafer being dynamically connected (e.g., clamped) to the ESC. Sensing the two vibrations can be done with laser light bounced back from the ESC and from the wafer, such as at the edge of wafer outside of the outer diameter of ESC.

Thus, a wafer detection system is provided wherein wafer detection is based on an acoustic impedance measurement. A wafer can be detected on a transfer arm, since the resonance frequency would be different by a weight of the wafer. The detection system can also be utilized to detect wafer clamping on an ESC. If the wafer is clamped, a wafer can be treated as a solid mass in conjunction with the ESC, but if not clamped, it may exhibit a different impedance pattern. At a specific frequency, a wafer may go into oscillation with a phase shift, and an impedance may be different. For example, acoustic impedance can be measured with a relatively small speaker (e.g., a speaker without a cone). Due at least in part to back-EMF, voltage under constant current drive can dramatically change around resonance. The present disclosure can be utilized as an alternative to, or a backup to, a capacitance measurement method. Ultrasonic imaging can be further used for reliable wafer detection.

Although the invention has been shown and described with respect to a certain embodiment or embodiments, it should be noted that the above-described embodiments serve only as examples for implementations of some embodiments of the present invention, and the application of the present invention is not restricted to these embodiments. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application. Accordingly, the present invention is not to be limited to the above-described embodiments, but is intended to be limited only by the appended claims and equivalents thereof.

The invention claimed is:

1. A workpiece clamping status detection system, comprising:
    a clamping device having a clamping surface, wherein the clamping device is configured to selectively clamp a workpiece to the clamping surface;
    a vibration-inducing mechanism that is not in physical contact with the clamping device, wherein the vibration-inducing mechanism is configured to selectively vibrate one or more of the clamping device and workpiece via an emission of sound waves from the vibration-inducing mechanism;
    a vibration-sensing mechanism that is not in physical contact with the clamping device, wherein the vibration-sensing mechanism is configured to detect the vibration of the one or more of the clamping device and workpiece; and
    a controller configured to determine a clamping state associated with the clamping of the workpiece to the clamping surface, wherein the clamping state is associated with the detected vibration of the one or more of the clamping device and workpiece.

2. The workpiece clamping status detection system of claim 1, wherein the vibration-inducing mechanism comprises an acoustic device.

3. The workpiece clamping status detection system of claim 2, wherein the acoustic device comprises vibration transmitter comprising an audio speaker.

4. The workpiece clamping status detection system of claim 2, wherein the vibration-sensing mechanism comprises an accelerometer comprising a microphone.

5. The workpiece clamping status detection system of claim 1, wherein the vibration-inducing mechanism comprises an ultrasound emitter, and wherein the vibration-sensing mechanism comprises an ultrasound receiver.

6. The workpiece clamping status detection system of claim 5, wherein the ultrasound transmitter and ultrasound receiver are defined by an ultrasound transducer.

7. The workpiece clamping status detection system of claim 1, wherein the controller is configured to differentiate an impedance pattern associated with the clamping state.

8. The workpiece clamping status detection system of claim 1, wherein the clamping device comprises an electrostatic clamp, and wherein the clamping surface comprises a generally planar surface configured to electrostatically clamp the workpiece thereto.

9. The workpiece clamping status detection system of claim 1, wherein the clamping device comprises a mechanical clamp.

10. The workpiece clamping status detection system of claim 9, wherein the mechanical clamp comprises one or more grippers configured to selectively grip a peripheral edge of the workpiece.

11. The workpiece clamping status detection system of claim 1, wherein a mass of the workpiece is less than a mass of the clamping device.

12. A method for detecting a clamping status of a workpiece in a clamping device, the method comprising:
    clamping a surface of the workpiece to a clamping surface of the clamping device;
    inducing a vibration within one or more of the clamping device and workpiece via an emission of sound waves from a vibration-inducing mechanism that is not in physical contact with the clamping device;
    detecting the vibration of the one or more of the clamping device and workpiece via a detection of a reflection of the sound waves; and
    determining a clamping state associated with the clamping of the workpiece to the clamping surface, wherein the clamping state is associated with a resonant frequency of the detected vibration of the one or more of the clamping device and workpiece.

13. The method of claim 12, wherein inducing the vibration within one or more of the clamping device and workpiece comprises emitting the sound waves toward one or more of the clamping device and workpiece.

14. The method of claim 13, wherein detecting the vibration of the one or more of the clamping device and workpiece comprises detecting the sound waves once the sound waves bounce off the one or more of the clamping device and workpiece.

15. The method of claim 12, wherein clamping the surface of the workpiece to the clamping surface of the clamping device comprises electrostatically clamping the surface of the workpiece to a generally planar surface of an electrostatic clamp.

16. The method of claim 12, wherein clamping the surface of the workpiece to the clamping surface of the clamping device comprises mechanically clamping a peripheral edge of the workpiece to via a mechanical clamp.

* * * * *